(12) United States Patent
Beger et al.

(10) Patent No.: US 8,313,513 B2
(45) Date of Patent: Nov. 20, 2012

(54) IMPLANT AND IMPLANT SYSTEM

(75) Inventors: Jens Beger, Tuttlingen (DE); Susanne Klingseis, Biberach (DE)

(73) Assignee: Aesculap AG, Tuttlingen (DE)

( * ) Notice: Subject to any disclaimer, the term of this patent is extended or adjusted under 35 U.S.C. 154(b) by 585 days.

(21) Appl. No.: 12/455,585

(22) Filed: Jun. 2, 2009

(65) Prior Publication Data

US 2009/0306716 A1 Dec. 10, 2009

Related U.S. Application Data

(63) Continuation of application No. PCT/EP2007/062862, filed on Nov. 27, 2007.

(30) Foreign Application Priority Data

Dec. 8, 2006 (DE) .......................... 10 2006 059 395

(51) Int. Cl.
A61B 17/70 (2006.01)

(52) U.S. Cl. .......................................... 606/249; 606/74

(58) Field of Classification Search .................. 606/246, 606/248, 249, 263, 74
See application file for complete search history.

(56) References Cited

U.S. PATENT DOCUMENTS

| | | | |
|---|---|---|---|
| 3,648,691 A | 3/1972 | Lumb et al. | |
| 5,047,055 A | 9/1991 | Bao et al. | |
| 5,192,326 A | 3/1993 | Bao et al. | |
| 5,456,722 A | 10/1995 | McLeod et al. | |
| 5,496,318 A * | 3/1996 | Howland et al. | 606/249 |
| 5,540,703 A | 7/1996 | Barker, Jr. et al. | |
| 5,609,634 A * | 3/1997 | Voydeville | 623/13.11 |
| 5,628,756 A | 5/1997 | Barker, Jr. et al. | |
| 5,645,599 A | 7/1997 | Samani | |
| 5,824,093 A | 10/1998 | Ray et al. | |
| 5,836,948 A | 11/1998 | Zucherman et al. | |
| 6,232,406 B1 * | 5/2001 | Stoy | 525/329.1 |
| 6,440,169 B1 | 8/2002 | Elberg et al. | |
| 6,514,256 B2 | 2/2003 | Zucherman et al. | |
| 6,602,291 B1 * | 8/2003 | Ray et al. | 623/17.11 |
| 6,626,944 B1 * | 9/2003 | Taylor | 623/17.16 |
| 6,695,842 B2 | 2/2004 | Zucherman et al. | |
| 6,733,534 B2 | 5/2004 | Sherman | |
| 6,761,720 B1 * | 7/2004 | Senegas | 606/249 |
| 7,238,204 B2 | 7/2007 | Le Couedic et al. | |
| 7,445,637 B2 | 11/2008 | Taylor | |
| 7,520,887 B2 | 4/2009 | Maxy et al. | |
| 2003/0144737 A1 | 7/2003 | Sherman | |

(Continued)

FOREIGN PATENT DOCUMENTS

EP 0 563 332 8/1995

(Continued)

*Primary Examiner* — Alvin Stewart
*Assistant Examiner* — Lynnsy Schneider
(74) *Attorney, Agent, or Firm* — Lipsitz & McAllister, LLC

(57) ABSTRACT

In order to improve an implant for the dorsal stabilization of a human or animal spinal column, comprising an attachment device for placing in position against and/or fixing to spinous processes of adjacent vertebrae of the spinal column, such that it can be used for the dynamic dorsal stabilization of the spinal column, it is suggested that the implant comprise at least one spacer element which is associated with the attachment device and designed in such a manner that it alters its external shape and/or its elastic properties as a result of a change in ambient conditions and/or forces acting on it.
Furthermore, an improved implant system for the dorsal stabilization of a human or animal spinal column is suggested.

47 Claims, 10 Drawing Sheets

U.S. PATENT DOCUMENTS

| | | |
|---|---|---|
| 2003/0220643 A1 | 11/2003 | Ferree |
| 2004/0024458 A1 | 2/2004 | Senegas et al. |
| 2004/0097931 A1 | 5/2004 | Mitchell |
| 2004/0106995 A1 | 6/2004 | Le Couedic et al. |
| 2004/0117017 A1 | 6/2004 | Pasquet et al. |
| 2004/0181282 A1 | 9/2004 | Zucherman et al. |
| 2004/0199255 A1 | 10/2004 | Mathieu et al. |
| 2004/0243239 A1 | 12/2004 | Taylor |
| 2005/0004674 A1 | 1/2005 | Senegas et al. |
| 2005/0010298 A1 | 1/2005 | Zucherman et al. |
| 2005/0033434 A1 | 2/2005 | Berry |
| 2005/0192581 A1* | 9/2005 | Molz et al. ............ 606/74 |
| 2005/0261768 A1 | 11/2005 | Trieu |
| 2005/0288672 A1 | 12/2005 | Ferree |
| 2006/0089719 A1* | 4/2006 | Trieu ............ 623/17.13 |
| 2006/0217726 A1 | 9/2006 | Maxy et al. |
| 2006/0235532 A1 | 10/2006 | Meunier et al. |
| 2006/0271044 A1* | 11/2006 | Petrini et al. ............ 606/61 |
| 2007/0191838 A1* | 8/2007 | Bruneau et al. ............ 606/61 |
| 2007/0213829 A1 | 9/2007 | Le Couedic et al. |
| 2007/0270823 A1* | 11/2007 | Trieu et al. ............ 606/61 |
| 2008/0114357 A1* | 5/2008 | Allard et al. ............ 606/61 |
| 2008/0262619 A1* | 10/2008 | Ray ............ 623/17.11 |
| 2009/0030523 A1 | 1/2009 | Taylor |

FOREIGN PATENT DOCUMENTS

| | | |
|---|---|---|
| EP | 1 138 268 | 10/2001 |
| EP | 1 330 987 | 7/2003 |
| FR | 2 717 675 | 9/1995 |
| FR | 2 768 612 | 3/1999 |
| FR | 2 816 197 | 5/2002 |
| WO | 94/26192 | 11/1994 |
| WO | 02/03882 | 1/2002 |
| WO | 03/015646 | 2/2003 |
| WO | 2004/064693 | 8/2004 |
| WO | 2004/073532 | 9/2004 |
| WO | 2004/073533 | 9/2004 |
| WO | 2004/084743 | 10/2004 |
| WO | 2005/115261 | 12/2005 |
| WO | 2006/106246 | 10/2006 |

* cited by examiner

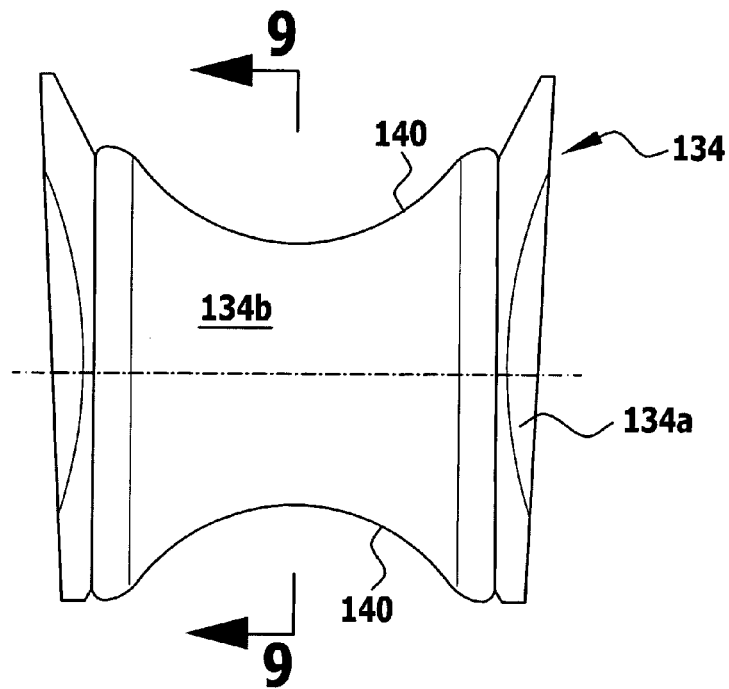
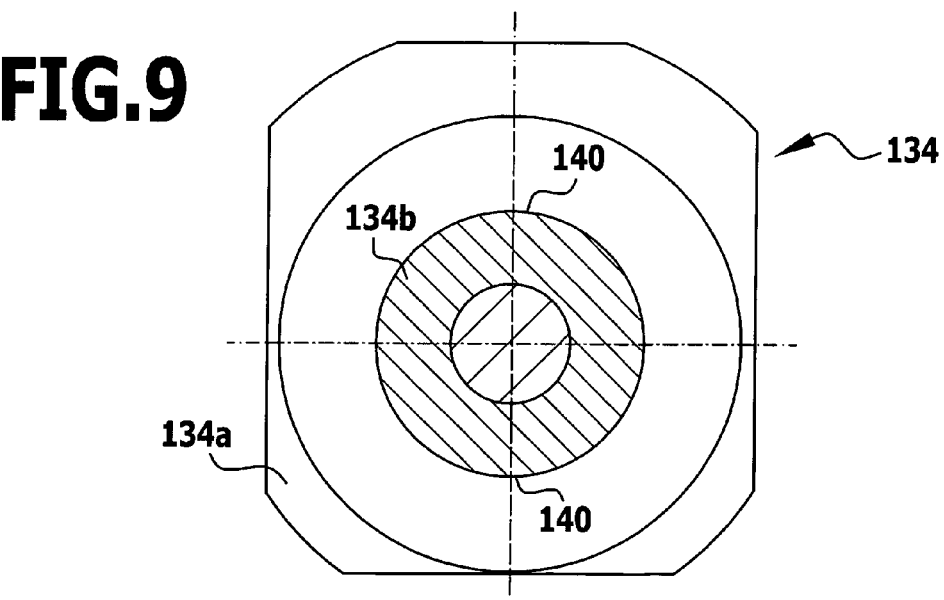

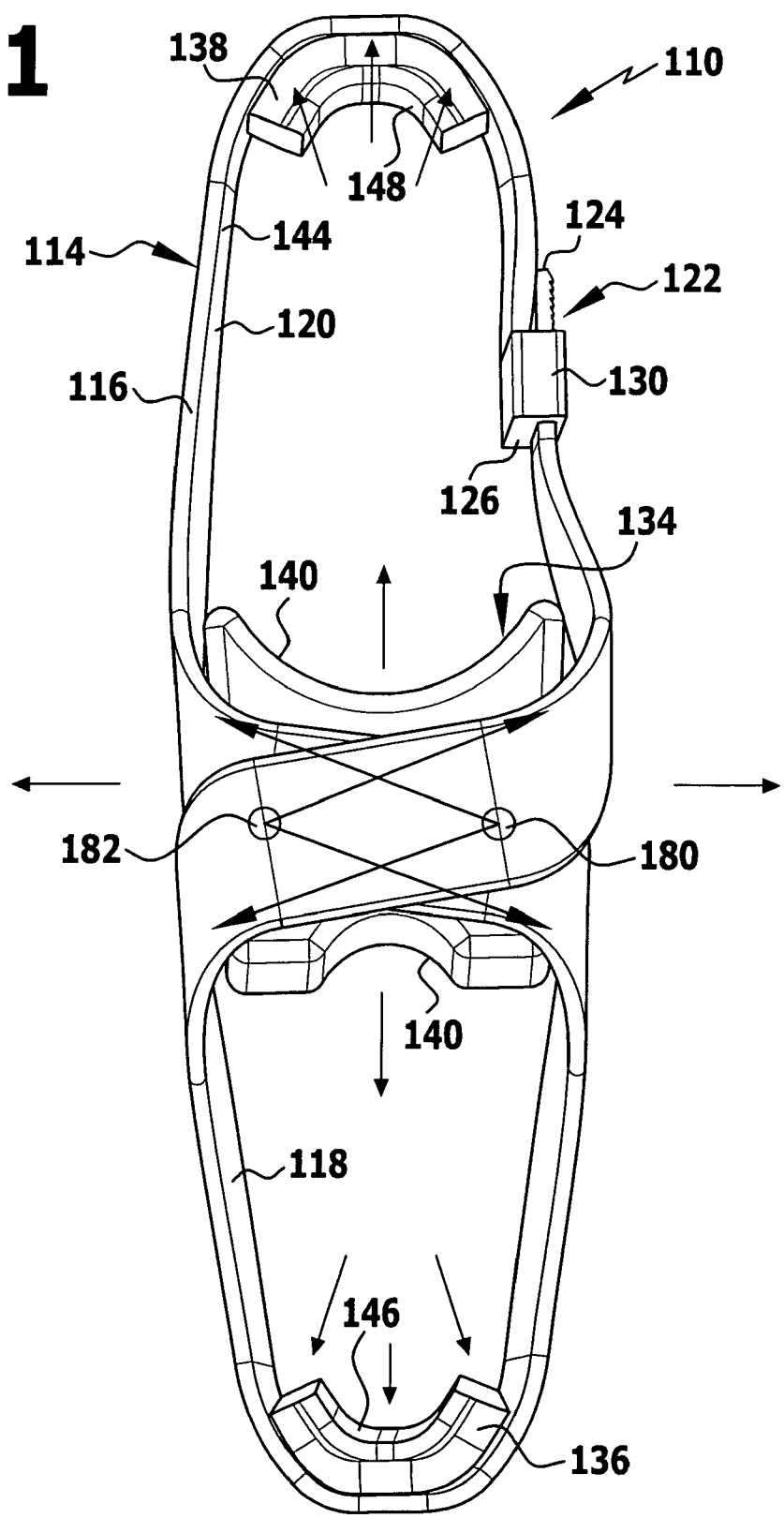

IMPLANT AND IMPLANT SYSTEM

This application is a continuation of international application number PCT/EP2007/062862 filed on Nov. 27, 2007.

The present disclosure relates to the subject matter disclosed in international application number PCT/EP2007/062862 of Nov. 27, 2007 and German application number 10 2006 059 395.2 of Dec. 8, 2006, which are incorporated herein by reference in their entirety and for all purposes.

FIELD OF THE INVENTION

The present invention relates to an implant generally, and more specifically to an implant for the dorsal stabilization of a human or animal spinal column.

Moreover, the present invention relates to an implant system generally, and more specifically to an implant for the dorsal stabilization of a human or animal spinal column.

Furthermore, the present invention relates to a method for the stabilization of a human or animal spinal column generally, and more specifically to a method for the dorsal stabilization of a human or animal spinal column with an implant.

BACKGROUND OF THE INVENTION

The present invention relates to an implant for the dorsal stabilization of a human or animal spinal column, comprising an attachment device for placing in position against and/or fixing to spinous processes of adjacent vertebrae of the spinal column.

Furthermore, the present invention relates to an implant system for the dorsal stabilization of a human or animal spinal column with at least one implant for the dorsal stabilization of the spinal column, comprising an attachment device for placing in position against and/or fixing to spinous processes of adjacent vertebrae of the spinal column with instrumentation for inserting the implant into a human or animal body.

An implant of the type described at the outset is known, for example, from U.S. Pat. No. 6,695,842. Its purpose is the static, dorsal stabilization of the spinal column. For this purpose, it is fixed to spinous processes of adjacent vertebrae of the spinal column and keeps them at a predetermined distance, in particular, in order to relieve pressure on an intervertebral disk arranged between the two vertebrae. Implants of this type are inserted following operations on intervertebral disks, in particular, or serve as additional stabilization following the removal of an intervertebral disk and subsequent fusion of adjacent vertebrae to one another.

The known implant is not, however, suitable for successively accustoming an intervertebral disk, which has been treated operatively, to natural strain again. It can either stabilize two vertebrae relative to one another or completely free the two vertebrae once the implant has been removed. As a result, either a complete relieving of pressure on the intervertebral disk or a complete load on the intervertebral disk is brought about when an implant is present and after it has been removed, respectively.

It is, therefore, an object of the present invention to improve an implant and an implant system of the type described at the outset such that they can be used for the dynamic dorsal stabilization of the spinal column.

SUMMARY OF THE INVENTION

In a first aspect of the invention, an implant for the dorsal stabilization of a human or animal spinal column, comprises an attachment device for placing in position against and/or fixing to spinous processes of adjacent vertebrae of the spinal column. Moreover, the implant comprises at least one spacer element associated with the attachment device and designed in such a manner that it alters its external shape and/or its elastic properties as a result of a change in ambient conditions and/or forces acting on it.

In a second aspect of the invention, an implant system for the dorsal stabilization of a human or animal spinal column comprises at least one implant for the dorsal stabilization of the spinal column. The at least one implant comprises an attachment device for placing in position against and/or fixing to spinous processes of adjacent vertebrae of the spinal column and instrumentation for inserting the implant into a human or animal body. Moreover, the implant comprises at least one spacer element designed in such a manner that it alters its external shape and/or its elastic properties as a result of a change in ambient conditions and/or forces acting on it.

In a third aspect of the invention, a method for the dorsal stabilization of a human or animal spinal column with an implant as defined in accordance with the first aspect of the invention or an implant system as defined in accordance with the second aspect of the invention, wherein an access to the human or animal body is opened up and the implant is introduced into the body with a spacer element dehydrated at least partially and the attachment device is placed in position against spinous processes of two adjacent vertebrae and connected to them at least loosely

BRIEF DESCRIPTION OF THE DRAWINGS

The foregoing summary and the following description of preferred embodiments of the invention may be better understood in conjunction with the drawings, of which:

FIG. 8: shows a side view of the spacer element illustrated in FIGS. 6 and 7;

FIG. 9: shows a cross-sectional view of the spacer element from FIG. 8 along line 9-9;

FIG. 11: shows a side view of the implant from FIG. 6.

DETAILED DESCRIPTION OF PREFERRED EMBODIMENTS OF THE INVENTION

Figure 1:
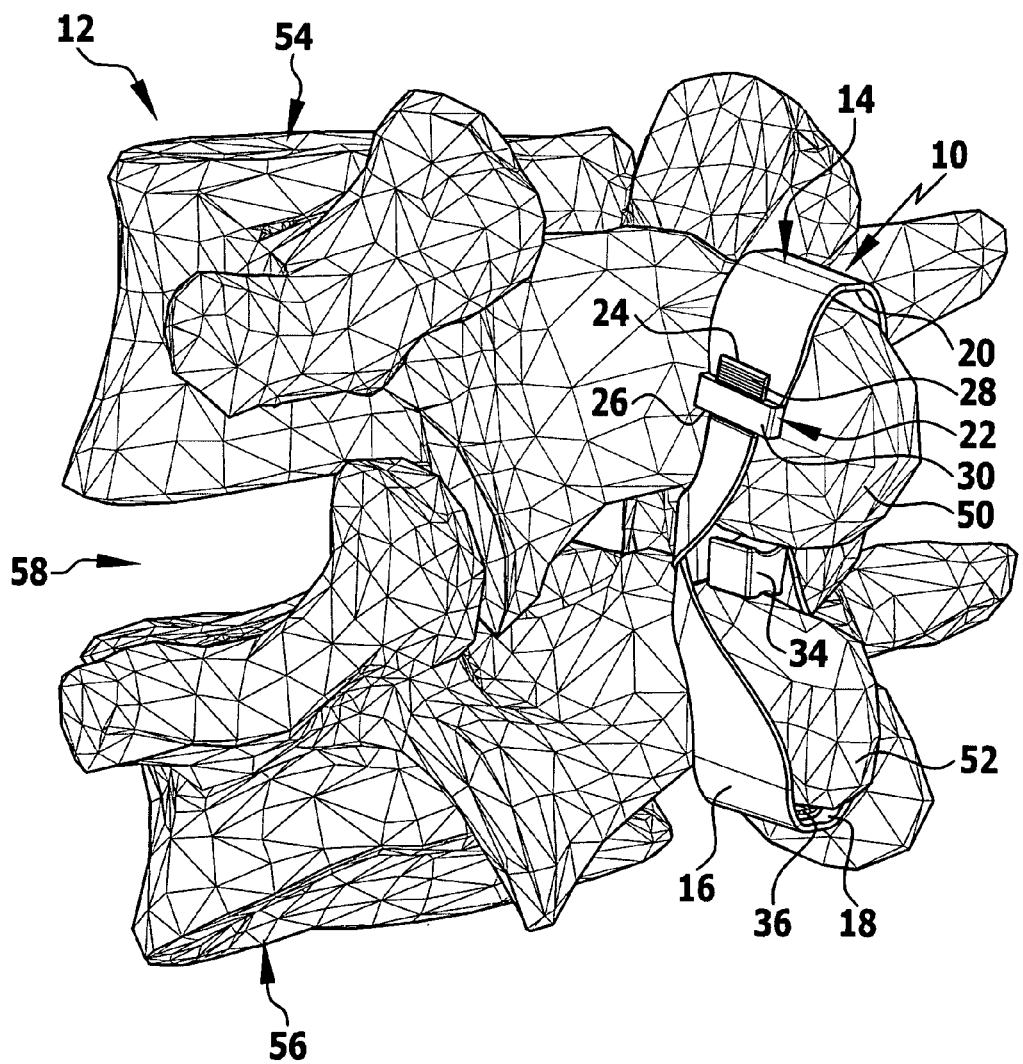
FIG. 1: shows a first embodiment of an implant placed in position against two spinous processes of adjacent vertebrae with spacer elements in the implantation position.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to an implant for the dorsal stabilization of a human or animal spinal column, comprising an attachment device for placing in position against and/or fixing to spinous processes of adjacent vertebrae of the spinal column, wherein the implant comprises at least one spacer element associated with the attachment device and designed in such a manner that it alters its external shape and/or its elastic properties as a result of a change in ambient conditions and/or forces acting on it.

It is possible with an implant of this type to achieve a balance between mobility of the vertebrae, which are connected to one another and define a motion segment, and stabilization. In particular, it makes a restriction of the movement of adjacent vertebrae possible, namely in extension and/or flexion, depending of the configuration. The mobility which can be predetermined by the implant can be adapted, in particular, to changes in ambient conditions. For example, changes in ambient conditions which are suitable in this respect are changes in humidity, changes in pressure, changes in temperature, changes in pH values and additional changes in biological, chemical and/or physical parameters in the surroundings of the implant. Restrictions in movement may be achieved by changes in shape and/or changes in elastic properties of the at least one spacer element, for example, its modulus of elasticity. The more elastic the spacer element, the greater the mobility of the vertebrae which are connected to one another and vice versa. Furthermore, the spacer element can also absorb loads which act on the vertebrae as a result of movement of the body. A relief of pressure on the intervertebral disk between the vertebrae may be achieved, altogether, with the attachment device. A regeneration of the intervertebral disk is stimulated by the dynamic dorsal stabilization. The implant suggested can be fixed, in particular, to spinous processes of two adjacent vertebrae, wherein tensioning of the implant on the spinous processes following implantation can be achieved by means of the at least one spacer element. Furthermore, the implant has the advantage that it can react to physiological changes; for example, the spacer element can have a different shape and/or different elastic properties, which lead either to a greater stabilization or to a greater mobility of the vertebrae connected to one another, on account of forces which have different effects while resting and while walking, respectively. The mobility of the spinous processes relative to one another will be improved when the elasticity of the spacer element is increased. The stability of the connection between the adjacent vertebrae will be improved, on the other hand, when the elasticity of the spacer element is decreased.

The construction of the implant will be particularly simple when the spacer element is produced from a memory material. As a result, changes in shape may be specifically brought about on account of different ambient conditions, in particular, changes in shape as a result of changes in temperature and/or effective forces.

The memory material is preferably a metal or a plastic. Nickel-titanium (NiTi) which is also designated as Nitinol, copper-zinc (CuZn), copper-zinc-aluminum (CuZnAl), copper-zinc-nickel (CuZnNi) or iron-nickel-aluminum (FeNiAl) are suitable, in particular, as metals. In addition, plastic materials, for example, memory polymers can be used. They may be designed in such a manner that they resume their original shape, for example, as a result of heating up. One example for a plastic material which displays a one-way memory effect is a so-called memory foam which is produced from polyurethane with the addition of further chemicals. It is used, for example, for the production of mattresses. In addition, memory polymers can also have a reversible memory effect which is not controlled thermally but rather optically. In this respect, butyl acrylates are, in particular, conceivable which interlace at their side chains via cinnamic acid groups when irradiated with ultraviolet light of a wavelength suitable for this purpose and break the linking again when irradiated with light of a different wavelength. A one-sided irradiation of a component can, therefore, lead to a one-sided interlacing and, consequently, an anisotropic change in shape. In addition, magnetically induced memory polymers are also conceivable.

It is particularly advantageous when the spacer element can be hydrated. Such a spacer element has particularly favorable properties for allowing an adaptation of the implant to physiological changes in the motion segment. It is, in this respect, known for the height of the intervertebral disk to decrease during the course of a day under load due to dehydration. The rigidity of the implant can be adapted, for example, due to corresponding selection and shaping of one or more spacer elements so that an optimum relief can also be achieved as a result of physiological changes in the motion segment. In practice, this means that the elasticity of the spacer element is preferably adapted such that it decreases with an increasing pressure load which leads to stiffening and, therefore, to a greater stabilization of the motion segment. For example, the spacer element which can be hydrated can absorb water again when relieved of pressure, whereby it can become more elastic again, for example, which improves mobility of the motion segment. With implants of this type it is, therefore, possible to stop any further degeneration of a damaged intervertebral disk or even partially regenerate the intervertebral disk. This can be achieved, in particular, by an, again, improved hydration of the intervertebral disk as a result of it being relieved of pressure by the implant according to the invention.

The at least one hydratable spacer element is preferably produced at least partially from a hydrogel. Hydrogels are eminently suitable as spacer elements which can alter not only their shape but also their elastic properties as a result of physiological changes in the motion segment. Dehydrated hydrogels are less elastic, hydrated hydrogels, on the other hand, display a high elasticity. Furthermore, hydrogels can be hydrated irreversibly or also reversibly depending on their construction. Examples for hydrogels are known from U.S. Pat. No. 6,232,406 as well as U.S. Pat. No. 5,824,093 which are both incorporated herewith into the disclosure of the present application with their entire content. Hydrogels are defined, in particular, as soft, elastic, hydrophilic polymeric materials which can swell in water but are not soluble and the water content of which is at least 20% by weight. They are subdivided into two subclasses, namely degradable hydrogels and non-degradable hydrogels. Degradable hydrogels comprise functional groups which can be split hydrolytically or enzymatically. Non-degradable hydrogels generally consist of carbon chains which are not degradable in the body. The implant according to the invention is preferably produced from a non-degradable hydrogel. Examples of non-degradable hydrogels are high-molecular polyvinyl alcohol (PVAL), poly-2-hydroxyethyl methacrylate (PHEMA), acrylate copolymers as well as hydrophilic polyurethane.

In order to be able to insert the implant into a human or animal body as easily as possibly and preferably through a minimally invasive access, it is favorable when the at least one spacer element is dehydrated to a maximum in an implantation position of the implant, in which it can be inserted into a human or animal body.

The at least one spacer element is favorably designed in such a manner that it can be hydrated in the extracellular space of a human or animal body on account of osmotic pressure. The implant can be adapted to physiological changes, for example, as a result of changes in the spacer element. It can, in particular, be enriched with water present in the extracellular space and thus change its shape and/or its elastic properties.

In accordance with one preferred embodiment of the invention, it may be provided for the at least one spacer element to be designed in such a manner that it can be dehydrated at least partially as a result of pressure acting on it. It can preferably be dehydrated completely, wherein a complete dehydration, for example, of a hydrogel is to be understood such that the amount of water it loses is only as much as the amount it can absorb again. An at least partial dehydration as a result of pressure makes it possible to configure the implant such that the spacer element will become less elastic as a result of pressure acting on it and, therefore, stabilize a damaged motion segment of the spinal column to a greater extent. If the load is removed from the spacer element again, the spacer element can also absorb water again and, on the other hand, change its shape and/or its elastic properties.

In order to make the insertion and fixing of the implant to the spinal column easier, it is advantageous when the implant can be brought from an implantation position, in which it can be placed in position against at least one spinous process of a vertebra of the spinal column and/or be released from it, into a stabilizing position, in which it can be fixed to the at least one spinous process. In the implantation position, the implant is preferably shaped such that it can be introduced into a body through a minimally invasive access.

So that a permanent and stable fixing of the implant to vertebrae of a spinal column can be achieved, it is advantageous when the implant has at least one spinous process receptacle, in and/or at which at least one of two spinous processes of two adjacent vertebrae is held in the stabilizing position. Two spinous processes could also be held in the at least one spinous process receptacle, i.e., this could, in particular, be of such a size that two spinous processes can be inserted into it, for example, in the implantation position.

In order to make a secure connection between the implant and a spinous process possible in a simple manner, it is favorable when the at least one spinous process receptacle is open in the implantation position and closed in a ring shape in the stabilizing position. An implant designed in this manner can be fixed to vertebrae or to parts thereof, in particular, without the aid of additional attachment means such as, for example, bone screws or bone pins. For example, the spinous process receptacle can surround a spinous process in a ring shape and be tensioned on it.

The at least one spacer element preferably has at least one contact surface area for the spinous process and is designed in such a manner that the contact surface area for the spinous process abuts on at least one spinous process in the stabilizing position. It is, therefore, possible for a spinous process to abut directly on the at least one spacer element and be restricted in its movement by this element. The spacer element can, however, also tension the attachment device, in particular, on the spinous process, namely as a result of, for example, a change in shape and/or volume.

Two spinous process receptacles are advantageously provided. This makes it possible to fix each spinous process of the motion segment separately in a spinous process receptacle. As a result, stability of the implant is increased, on the one hand, and a permanent use of the implant improved, on the other hand.

In accordance with one preferred embodiment of the invention, it may be provided for a free cross-sectional surface area of the at least one spinous process receptacle to become smaller with increasing hydration of the at least one spacer element. In the case where one spinous process is inserted into the at least one spinous process receptacle, a reduction in the cross-sectional surface area preferably leads to the attachment device being tensioned on the spinous process.

It is favorable when the at least one spacer element separates two spinous process receptacles from one another. This means, in particular, that the at least one spacer element can be arranged between two spinous processes in an implantation position. As a result, the at least one spacer element can predetermine a distance between the two spinous processes directly or indirectly in a desired manner.

In order to be able to exploit the advantageous properties of the implant not only in extension but also flexion of a motion segment of the spinal column, it is favorable when at least two spacer elements are provided which are arranged at a spinous process receptacle so as to be located diametrically opposite one another. The spacer elements can, in particular, be arranged such that a spinous process held in the spinous process receptacle presses against the one spacer element during flexion of the motion segment and against the other spacer element during extension of the motion segment.

Three spacer elements are favorably provided. One can, in particular, be arranged such that it is located or held between two spinous processes after the implantation of the implant, the two other spacer elements at two spinous process receptacles provided for accommodating the spinous processes, each being preferably located diametrically opposite the spacer element arranged between the spinous processes. A desired, dynamic stabilization of the relevant motion segment of the spinal column can thus be achieved, depending on the design of the attachment device.

In order to be able to insert the implant easily into a human or animal body, in particular, through a minimally invasive access, it is advantageous when the at least one spacer element has, in a basic position, a volume which is at least 3 times smaller than a volume of the spacer element in a maximum expansion position. Furthermore, stabilization of a motion segment of the spinal column which is to be treated can, with such a spacer element, be achieved in practically any desired form.

The at least one spacer element is preferably dehydrated completely in the basic position and hydrated completely in the maximum expansion position. A transition between the basic position and the maximum expansion position can then be brought about by corresponding hydration or dehydration of the at least one spacer element.

In principle, it would be conceivable for the at least one spacer element to be deformable isotropically. The at least one spacer element is, however, preferably deformable anisotropically so that it alters its shape and/or an enclosed volume anisotropically as a result of a change in at least one ambient condition. In this way, restrictions on the mobility of the motion segment may be adjusted specifically with the implant according to the invention, namely, for example, dependent on physiological alterations at the motion segment.

It is possible in a simple manner, particularly when using a hydrogel, for the at least one spacer element which is deformable anisotropically to alter its shape and/or an enclosed volume anisotropically as a result of hydration.

The construction of the implant is simplified, in particular, when the at least one spacer element is symmetrically shaped. It may be symmetrically shaped not only in the implantation position but also in the stabilizing position. It is, however, also possible for the at least one spacer element to be symmetrically shaped only in one of the two specified positions.

The at least one spacer element is advantageously designed and arranged on the attachment device in such a manner that it limits movement towards one another of spinous processes which are connected to one another. This may be achieved, for example, in that the at least one spacer element is arranged between two spinous processes in the implantation position.

In principle, it would be conceivable to design the spacer element in one piece. The at least one spacer element does, however, advantageously comprise at last two spacer element parts. Such a spacer element makes it possible, in particular, in a simple manner to bring about an anisotropic change in shape as a result of altered ambient conditions. It would also be possible to form spacer element parts from different materials which react differently to altered ambient conditions, in particular, alter their shape and/or their elastic properties differently. As a result, desired stabilizing and/or movement requirements can be adjusted even more specifically with the implant.

The at least two spacer element parts can preferably be anisotropically hydrated differently so that they alter their shape and/or an enclosed volume anisotropically as a result of hydration. Anisotropically differently also means, in particular, that the at least two spacer element parts are of an identical design and, therefore, can also be anisotropically hydrated identically but anisotropy results, altogether, due to hydration or dehydration of the spacer element on account of a non-symmetric arrangement.

The at least two spacer element parts are preferably shaped and connected to one another in such a manner that they alter a shape and/or an enclosed volume in two directions which are linearly independent of one another as a result of hydration. For example, the attachment device can thus be tensioned specifically in different directions relative to a spinous process.

The construction of the spacer element will be particularly simple when the at least two spacer element parts are arranged in layers one on top of the other.

The at least two spacer element parts arranged in layers one on top of the other are preferably separated by layers of greater rigidity. As a result, anisotropy of the alteration in shape and/or volume and/or elasticity properties of the spacer element can be achieved in a desired manner.

In order to increase the stability of the spacer elements, in particular, their abrasion resistance for the case where they engage directly or indirectly on the locomotor system of the body, it is advantageous when the layers of greater rigidity comprise fabric layers and/or fiber-reinforced layers.

A spacer element which displays anisotropy of its properties in two directions independent of one another may be designed in a simple manner when a first spacer element part forms a core of the spacer element and when a second spacer element part surrounds the first spacer element part in a ring shape at least in sections. For example, the one spacer element part can be designed in the form of a cylindrical rod which is surrounded by a second, sleeve-like spacer element part. It would also be conceivable to design the first spacer element part in the form of a reel and to arrange the second spacer element part around a cylindrical core of the first spacer element part in the place of a wound thread in the case of a reel.

The construction of the at least one spacer element will be particularly simple when it is designed in the form of a cushion.

In order to make an ideal introduction of force into the at least one spacer element possible and to reduce any wear and tear thereof when it is in contact with the locomotor system, it is favorable when the at least one spacer element comprises a spacer element sleeve and a spacer element core and when the spacer element core alters its external shape and/or its elastic properties as a result of a change in ambient conditions and/or forces acting on it. The spacer element sleeve therefore serves, primarily, to protect the spacer element core. It may, however, also have an additional function, namely to predetermine a shape of the spacer element, preferably in a state expanded to the maximum. The spacer element sleeve can be designed to be non-elastic or alternatively elastic.

The spacer element sleeve is preferably produced from a fabric. A fabric makes it possible, in particular, for liquids, in particular, water to pass through. This is important, in particular, when the spacer element core is produced from a material which can be hydrated.

In order to increase the stability of the spacer element sleeve, this is favorably fiber-reinforced.

The construction of the implant will be particularly simple when the attachment device comprises at least one tape. For example, the attachment devices can be designed in the form of a tape which is closed in a ring shape and may be optionally opened for abutment on two spinous processes of adjacent vertebrae.

In order to be able to fix the implant permanently and securely on spinous processes of adjacent vertebrae, the at least one tape is designed to cross over and extend in the form of a double loop in the stabilizing position. The tape therefore wraps around the one and the other spinous process in the stabilizing position, wherein in the case of a single crossover of the tape the direction, in which the tape winds around the two spinous processes, alters, with a double crossover of the tape the direction, in which the tape winds around the spinous processes, remains the same. The at least one spacer element can be arranged, in particular, at the point where the tape crosses over once or several times. The tape is preferably fixed to the at least one spacer element.

In order to be able to introduce the implant easily and reliably into a human or animal body, the at least one tape is produced from a woven material. As a result, it is, in particular, also sufficiently flexible to be implanted in a minimally invasive manner.

In accordance with one preferred embodiment of the invention, the attachment device can be designed in the form of a tension strapping which limits movement away from one another of spinous processes which are connected to one another. Such a tension strapping allows, in particular, movement towards one another of spinous processes which are connected to one another, wherein the movement can, however, be limited, on the other hand, by the at least one spacer element.

It is advantageous when the attachment device has at least one closure device and when the at least one spinous process receptacle can be opened in the implantation position and closed in a ring shape in the stabilizing position with the at least one closure device. The closure device makes it possible in a simple manner, for example, to close a tape comprised by the attachment device in a ring shape or open it for implantation purposes.

The closure device is favorably designed in the form of a unidirectional closure device, in particular, in the form of a cable tie closure. This enables, for example, an attachment device opening in a ring shape, for example, in the form of a tape to be implanted and to loop around a spinous process. Closing and tensioning can be brought about with a unidirectional closure device in one step, namely by simple pulling.

Alternatively or in addition, it may be advantageous when the closure device comprises a press clip. As a result, a particularly secure connection of the two parts to be connected to one another for the purpose of closing the attachment device can be achieved.

To increase the stability of the implant, it is favorable when the at least one spacer element is connected non-detachably to the attachment device.

The invention also relates to an implant system for the dorsal stabilization of a human or animal spinal column with at least one implant for the dorsal stabilization of the spinal column, comprising an attachment device for placing in position against and/or fixing to spinous processes of adjacent vertebrae of the spinal column and instrumentation for inserting the implant into a human or animal body, wherein the implant comprises at least one spacer element designed in such a manner that it alters its external shape and/or its elastic properties as a result of a change in ambient conditions and/or forces acting on it.

An implant system of this type makes it possible, in particular, to stabilize a damaged motion segment of a human or animal spinal column dynamically and dorsally, as has already been described in detail above, in particular. The implant system preferably comprises one or more instruments, with the aid of which the implant can be inserted and fixed in a simple manner to spinous processes of adjacent vertebrae. Scalpels, clamps, scissors, needle holders, needles with sutures and the like are conceivable, in particular, as instruments. All the instruments can also be designed, in particular, as tubular shafted instruments, i.e., for a minimally invasive or percutaneous access.

In order to be able to adapt the implant system in a desired manner to the requirements found each time in conjunction with a dynamic dorsal stabilization of a motion segment of a human or animal spinal column, it is advantageous when the implant is one of the implants described above.

In addition, the invention relates to a method for the dorsal stabilization of a human or animal spinal column with one of the implants described above or one of the implant systems described above, with which an access to the human or animal body is opened up and
the implant is introduced into the body with a spacer element dehydrated at least partially and the attachment device is placed in position against spinous processes of two adjacent vertebrae and connected to them at least loosely.

This simple method makes a dynamic stabilization of a motion segment of a spinal column possible using the implants and implant systems, respectively, as described.

In accordance with one preferred variation of the method according to the invention, a minimally invasive access is opened up. In this way, operation trauma can be minimized and the healing process considerably improved following the implantation.

A first embodiment of an implant for the dynamic dorsal stabilization of a human spinal column 12 is illustrated in FIGS. 1 to 4 and provided, altogether, with the reference numeral 10. It comprises an attachment device 14 in the form of a crossover tape 16 which is laid essentially in the form of an "8".

The tape 16 laid or looped in the form of an "8" defines two spinous process receptacles 18 and 20 which are closed essentially in the shape of a ring. A closure device 22 is provided for closing the tape in the shape of a ring and connects free ends 24 and 26 of the tape 16 to one another. In the embodiment illustrated in FIGS. 1 to 4, the closure device 22 is designed in the form of a unidirectional closure device, namely in the form of a cable tie closure. For this purpose, the free end 24 is provided on one side with teeth 28 formed transversely to a longitudinal direction of the tape 16. A locking member 30 in the shape of a parallelepiped is placed on the other free end 26 and has an opening 32 which extends in longitudinal direction and in which a snap-in member, which is not illustrated, engages in the teeth 28 and is mounted in an elastic manner, is arranged. The opening 32 is dimensioned such that the free end 24 provided with the teeth 28 can be pushed through the opening 32. The free ends 24 and 26 are secured relative to one another by the snap-in member which is not illustrated and engages in the teeth 28. Furthermore, tension on the tape 16 can be increased by subsequently pulling the free end 24 out of the locking member 30, whereby the spinous process receptacles 18 and 20 become somewhat smaller in diameter or their free cross-sectional surface areas.

Three spacer elements 34, 36 and 38 are associated, altogether, with the attachment device 14. The spacer element 34 is of an approximately cube-shaped design and produced from a hydrogel, for example, a high-molecular polyvinyl alcohol (PVAL). The hydrogel is, in this respect, non-degradable. Channel-like recesses 40 and 42 which are aligned parallel to one another are provided on an upper and a lower side of the spacer element 34. The spacer element 34 is, in addition, attached on an inner side 44 of the tape 16. The recesses 40 and 42 point in the direction towards the spinous process receptacles 18 and 20. In practice, the spacer element 34 delimits the two spinous process receptacles 18 and 20 since it is arranged directly between them. The spacer elements 36 and 38 which are essentially flat and shaped like parallelepipeds are arranged at oppositely located ends of the spinous process receptacles 18 and 20 and are likewise provided with flat, channel-like recesses 46 and 48, respectively, which are each aligned parallel to the recesses 40 and 42 of the spacer element 34. The recesses 40, 42, 46 and 48 define contact surface areas for the spinous processes which are in contact with spinous processes 50 and 52 after implantation of the implant 10. The spacer elements 36 and 38 are also each formed from a hydrogel. One essential property of the hydrogel is that it can absorb water and, as a result, drastically increase its volume; in particular, it is possible for a hydrogel, which is dehydrated to the maximum and still has a water content of approximately 20% by weight, to have a volume in the dehydrated state which corresponds approximately to ¹⁄₁₀ to ¹⁄₂₀ of its volume in a state of maximum hydration. In any case, the spacer elements 34, 36 and 38 are designed in such a manner that they alter their external shape and/or their elastic properties as a result of a change in ambient conditions. The elastic properties of a hydrogel alter in accordance with its hydration. The more water a hydrogel has absorbed the more elastic it will be. As a result, it is the least elastic in its state of maximum dehydration.

For the dynamic dorsal stabilization of a motion segment of the spinal column 12, the implant 10 is secured to the spinous processes 50 and 52 of adjacent vertebrae 54 and 56. For this purpose, a minimally invasive access to the body of the patient will preferably be opened up. The tape 16 which is not yet closed upon itself is then inserted and, when seen dorsally, placed in the form of an "8" around the spinous processes 50 and 52. Proceeding from the free end 26, it is looped around the upper spinous process 50 in a clockwise direction and guided through between the spinous process 50 and the spinous process 52. The spacer element 34 attached to the inner side 44 is then seated exactly between the two spinous processes 50 and 52. The tape 16 is then looped around the lower spinous process 52 of the vertebra 56 in a counterclockwise direction and crosses over itself behind the spacer element 34. It is then guided further in a clockwise direction with its free end 24 as far as the free end 26 and connected to it by means of the closure device 22. The spinous processes 50 and 52 therefore penetrate the spinous process receptacles 20 and 18, respectively.

The tape 16, which is produced from a woven, biodegradable or also non-degradable material, will not be tensioned as narrowly or securely as possible around the spinous processes 50 and 52. On the contrary, it is placed essentially loosely around them. On account of an osmotic pressure prevailing in the extracellular space of the patient's body, the spacer elements become fully soaked with water after the implant 10 has been inserted, i.e., they are hydrated. Proceeding from an implantation position, in which the spacer elements 34, 36 and 38 are dehydrated, preferably dehydrated to the maximum, they have a volume following the hydration which is greater by approximately 3 times to 20 times than in the implantation position of the implant illustrated in FIGS. 1, 3 and 4. As a result of the increase in volume of the spacer elements 34, 36 and 38, the attachment device 14 is tensioned on the spinous processes 50 and 52. The implant 10 is now in its stabilizing position illustrated in FIG. 2.

Figure 2:
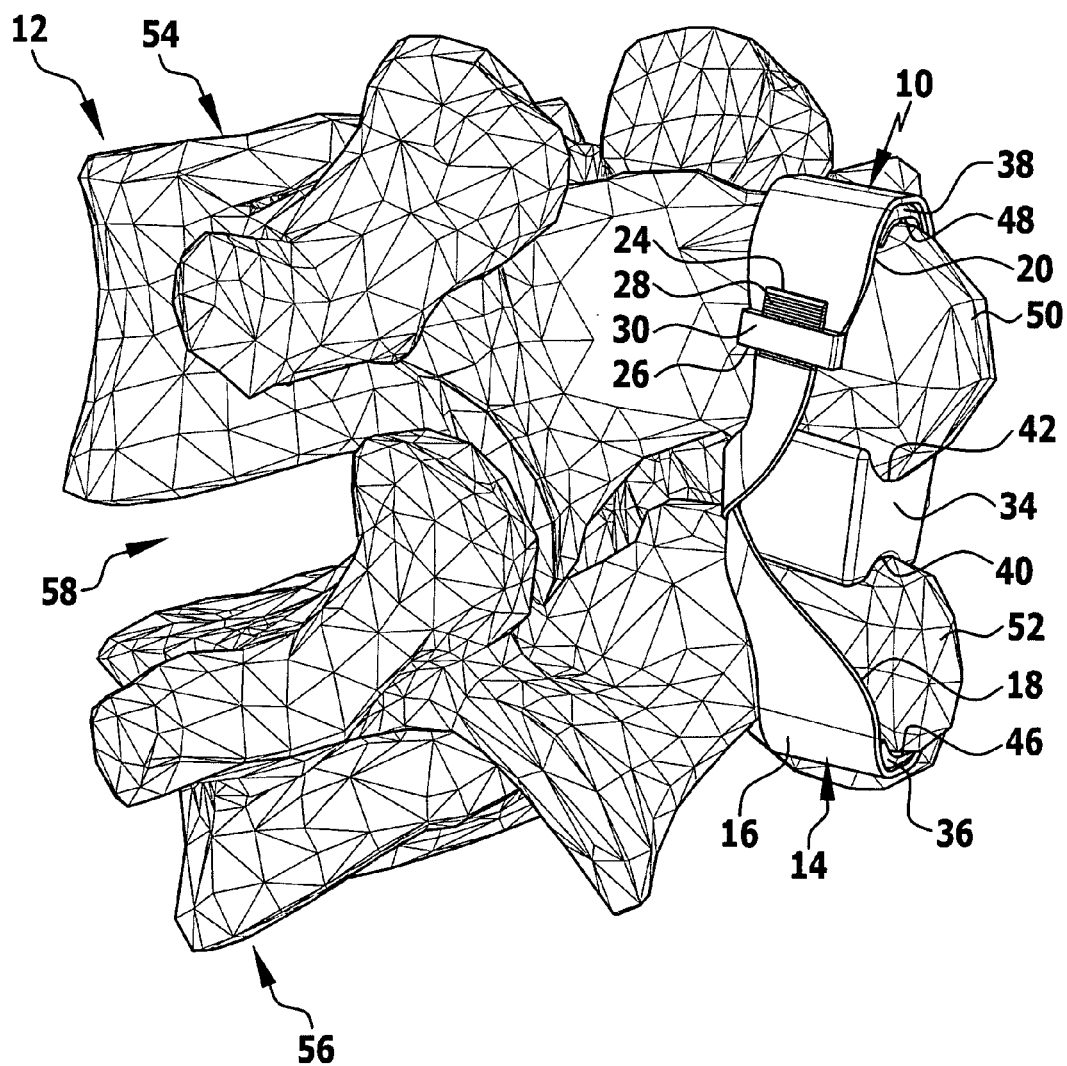
FIG. 2: shows a view similar to FIG. 1 but with spacer elements in the stabilizing position.
Figure 3:
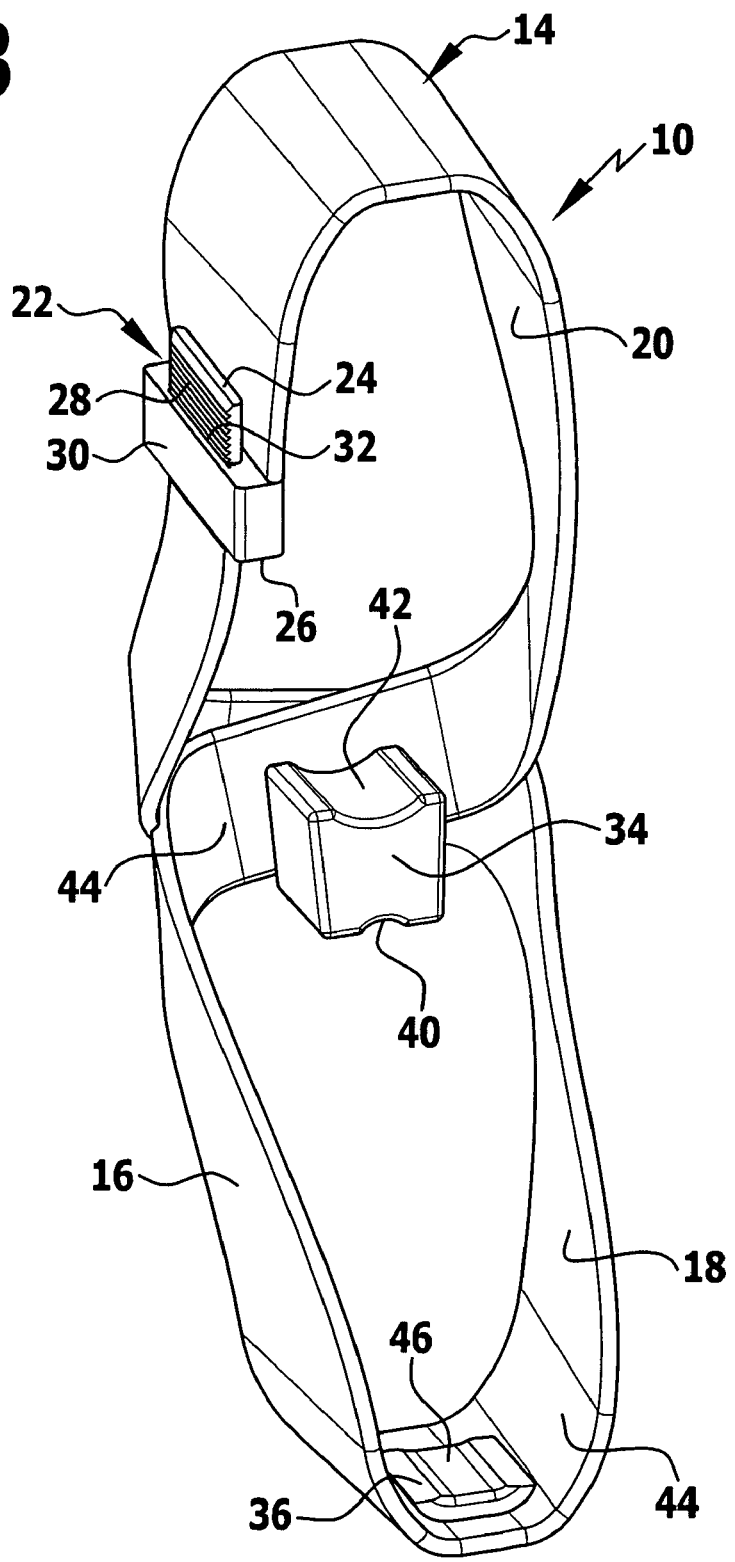
FIG. 3: shows a perspective view of the implant from FIG. 1 dorsally in the implantation position.
Figure 4:
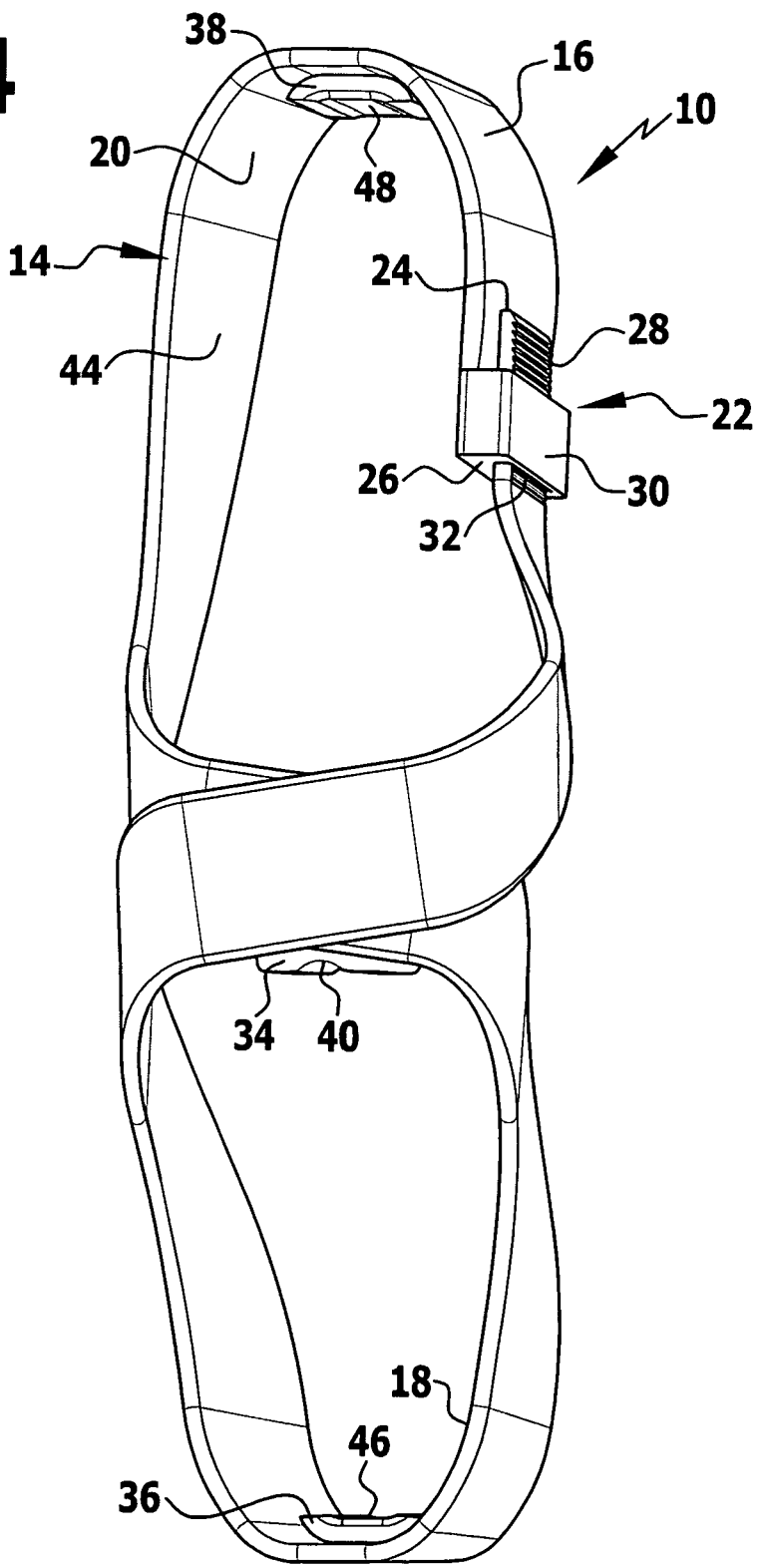
FIG. 4: shows a perspective rear view of the implant from FIG. 3.

On account of the use of spacer elements 34, 36 and 38 which are designed in such a manner that they alter their external shape and/or their elastic properties as a result of a change in ambient conditions and/or forces acting on them, it is possible with the implant 10 to stabilize the motion segment of the spinal column 12 defined by the two vertebrae 54 and 56 as well as the intervertebral disk, which is arranged in an intervertebral space 58 but not illustrated in FIGS. 1 and 2, dynamically and dorsally. Such an operation is suitable, for example, for relieving pressure on a partially degenerated intervertebral disk or for the temporary stabilization following an operation on the intervertebral disk, for example, following a partial resection thereof as a result of a prolapse of the intervertebral disk.

As a result of the attachment device 14 which forms a tension strapping, the tape 16 with the spacer elements 36 and 38 prevents too great a flexion of the motion segment, i.e., movement of the vertebrae 54 and 56 towards one another, during which the intervertebral disk is compressed. The hydrated spacer elements 36 and 38 act as cushioning members during any extension movement of the motion segment.

In contrast hereto, the intervertebral disk between the vertebrae 54 and 56 is relieved of pressure during any extension, i.e., any stretching movement of the spinal column 12. Consequently, the two spinous processes 50 and 52 move towards one another and attempt to compress the spacer element 34 held between them. The spacer element 34 serves, on the one hand, as a stop for the spinous processes 50 and 52 but, on the other hand, also as a cushioning element. On account of the pressure exerted on it, it discharges water again at least partially and cushions the movement of the spinous processes 50 and 52 towards one another in the hydrated state on account of its elastic properties. As a result of the partial dehydration on account of the pressure exerted by the spinous processes 50 and 52 on the spacer element 34, this will, however, become ever more inelastic, whereby a minimum distance between the two spinous processes 50 and 52 is defined. At the same time, it is, however, made possible for the spacer elements 36 and 38 to absorb water and so they are relieved of pressure during an extension movement of the spinal column 12 since a pressure load acting on the spinal column 12 is considerably less during an extension movement than during a flexion movement which likewise leads to a dehydration of the spacer elements 36 and 38, whereby their volume and their elasticity are reduced. Altogether, the implant 10 is, therefore, suitable for a targeted restriction of movement of the relevant motion segment.

Furthermore, the implant 10 is suitable for adaptation to physiological changes in the motion segment. During the course of a day, the height of the intervertebral disk is reduced under load as a result of dehydration. Consequently, the spinous processes 50 and 52 also press on the spacer element 34 in an increased manner and so this will be dehydrated under load and will become increasingly rigid. As a result, the implant 10 relieves the pressure on the intervertebral disk. During the night, the spacer element 34 can also be relieved of pressure again due to movement of the spinous processes 50 and 52 away from one another as a result of hydration of the intervertebral disk in the state relieved of pressure.

The implant 10 will preferably be introduced dorsally, as illustrated in FIGS. 1 and 2, namely in such a manner that the spacer element 34 is held back by the tape 16 on the ventral side. This prevents the spacer element 34 from being able to exert pressure on the spinal channel in the most unfavorable case. The tape 16 therefore serves at the same time as an expansion limitation for the spacer element 34 which can, however, expand in a dorsal direction as a result of hydration, as illustrated, for example, in FIG. 2.

The spacer elements 34, 36 and 38 can be stuck to the tape 16 or comprise a spacer element core consisting of a hydrogel which is placed in a pocket which can, in particular, be stuck, stitched or connected in any other optional manner to the tape 16. The pocket which forms a spacer element sleeve serves, in particular, to protect the actual hydrogel which can become worn as a result of direct abutment on the spinous processes 50 and 52. The spacer element sleeve can be produced, in particular, from a knitted or woven fabric which is preferably fiber-reinforced. All possible types of fiber which are biocompatible and not degradable are conceivable in this case. It would, of course, also be conceivable to use degradable hydrogels or an implant produced altogether from biodegradable materials. This would have the advantage, in particular, that no further surgical procedure to remove the implant again would be necessary in the case of a stabilization of the motion segment which is only temporarily desired. The hydrogels which are described in "Degradable hydrogels. Chen, Jun; Jo, Seongbong; Park, Kinam: Drug Targeting Delivery (1997), 7 (Handbook of Biodegradable Polymers), pages 203 to 230", can be considered, in particular, as biodegradable hydrogels.

This publication is herewith incorporated into the present application with its entire disclosure.

Figure 5:
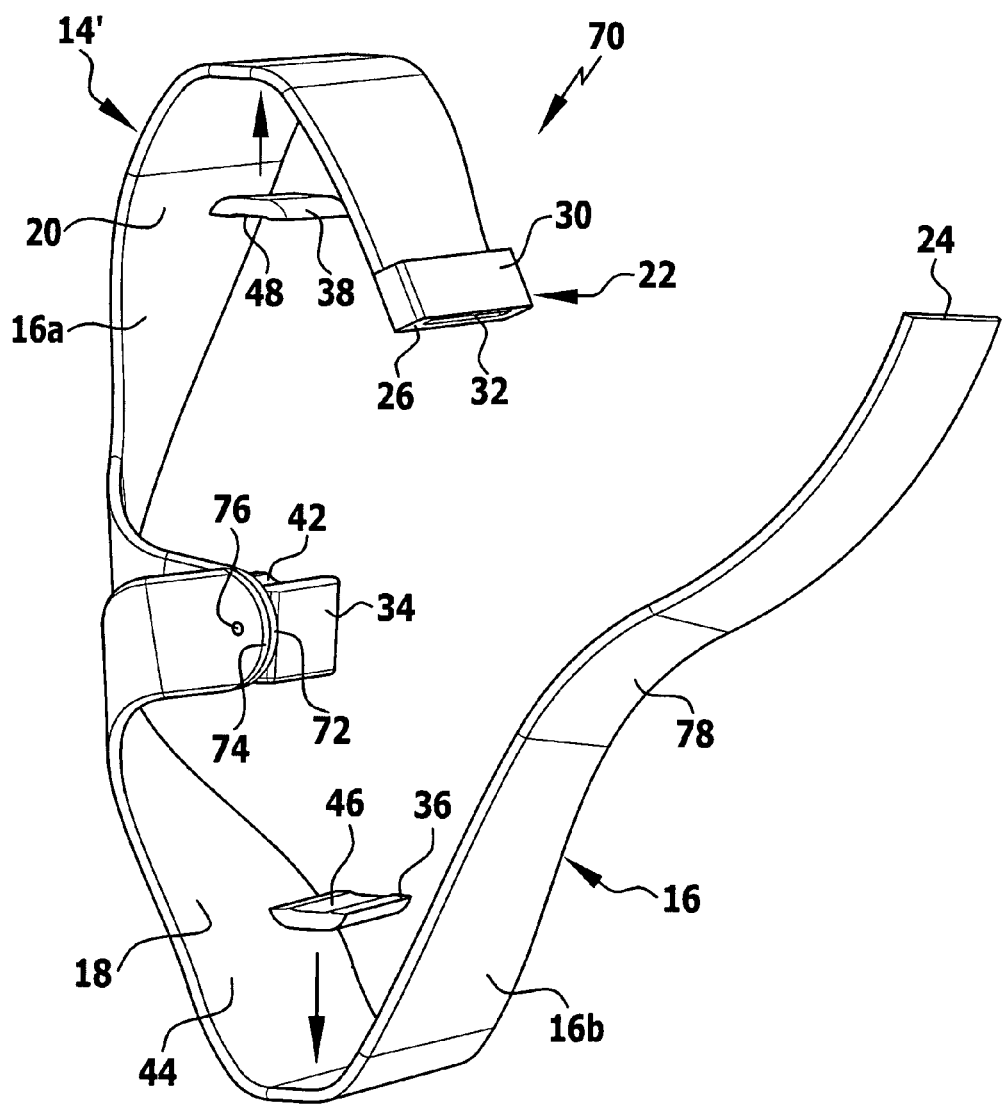
FIG. 5: shows a perspective view of a second embodiment of an implant.
Figure 6:
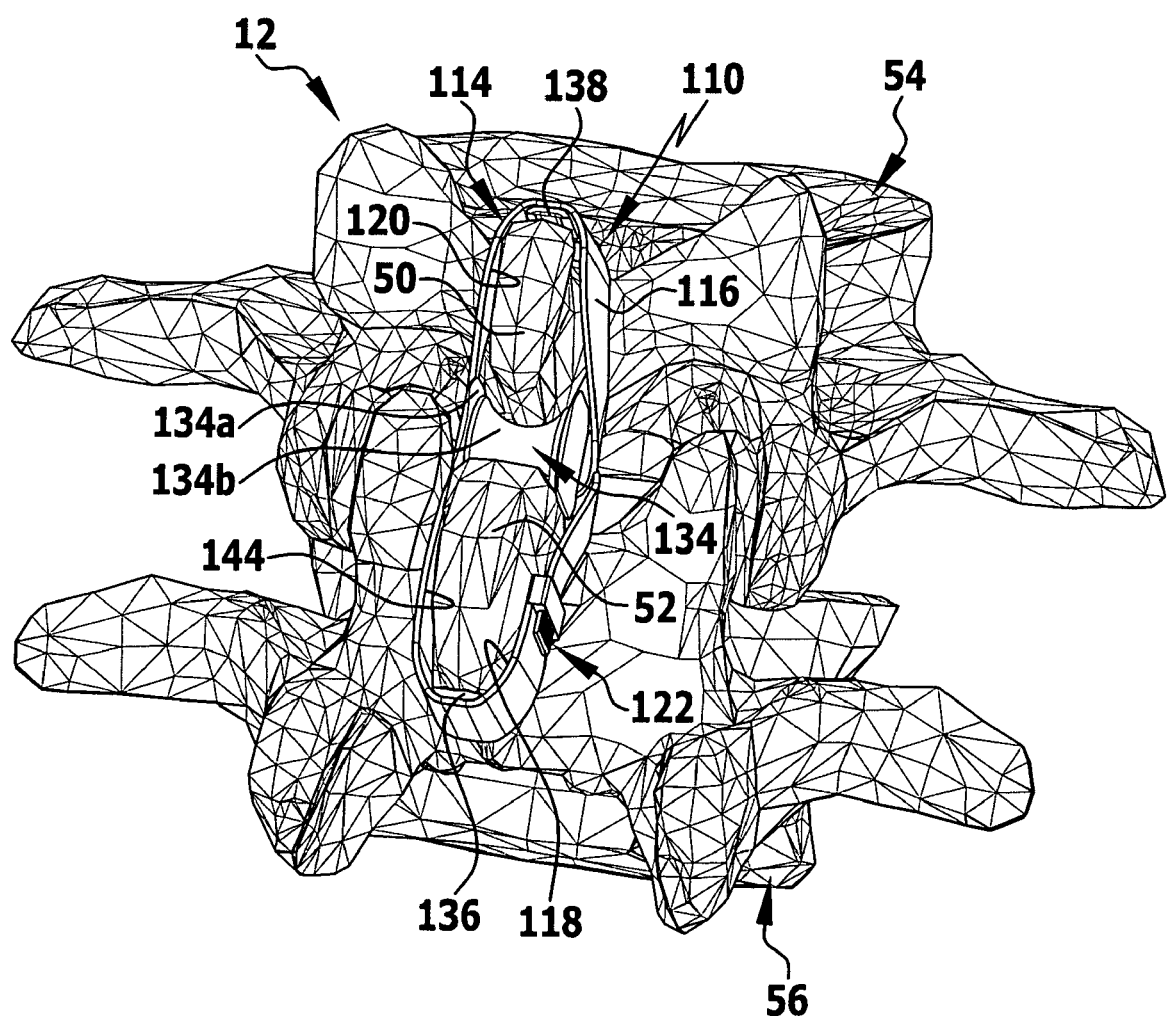
FIG. 6: shows a perspective view of a third implant placed in position against two spinous processes of adjacent vertebrae with spacer elements in the stabilizing position.

A variation of the implant 10 is illustrated in FIG. 5. Since it corresponds essentially to the implant 10, the same elements are provided with the same reference numerals.

The implant 70 illustrated in FIG. 5 differs from the implant 10 in the construction of the attachment device 14. The attachment device 14' of the implant 70 is likewise formed by a tape 16 which is, however, designed in two parts. An upper tape part 16a serves to form a spinous process receptacle 20. It has a first free end 26 which is provided with a locking member 30 which has an opening 32, at which a clamping mechanism, which is not illustrated, is provided in the interior. The upper tape part 16a has a length which can essentially enclose 270° of a spinous process 50. A spacer element 34, which corresponds to the spacer element 34 of the implant 10, is arranged on an inner side at the other free end 72 of the upper tape part 16a.

The end 72 is connected on its outer side to an inner side of a free end 74 of a lower tape part 16b. A connecting pin 76 or a rivet serves this purpose, in particular. It would also be conceivable to stick or to stitch the ends 72 and 74 together.

The lower tape part 16b is longer than the upper tape part 16a and so it can completely enclose the lower spinous process 52 of the vertebra 56. In addition, it has a second free end 24 which is designed in such a manner that it can be inserted through the opening 32 of the locking member 30 and be connected to it, for example, by clamping. In order to achieve a similar tension strapping to that of the implant 10, a tape section 78 of the lower tape part 16b, which is arranged approximately at the level of the spacer element 34 once the free end 24 has been connected to the free end 26, will preferably be connected either to the spacer element or to the free ends 72 and/or 74 of the upper tape part 16a and the lower tape part 16b, respectively. After the tape section 78 has been connected, for example, to the free ends 72 and/or 74, the implant 70 has a shape which corresponds essentially to that of the implant 10. Upper and lower spinous process receptacles 20 and 18 are separated by the spacer element 34 and, in addition, opposite the spacer element 34, are delimited by spacer elements 36 and 38 which are arranged on an inner side 44 of the tape 16 and are designed in accordance with the spacer elements 36 and 38 of the implant 10. This results in a functionality of the implant 70 which corresponds to that of the implant 10 and so reference can be made to the description above.

As a result of the two-part design of the tape 16, the placement of the attachment device 14 in position against the two spinous processes 50 and 52 is made easier, on the one hand, but, on the other hand, it should be taken into account that the tape section 78 must still be connected to the free ends 72 and/or 74 to form a desired tension strapping. Depending on the desired treatment situation, the implant 10 or alternatively the implant 70 can be used for the dynamic dorsal stabilization of a motion segment of the spinal column 12.

A third embodiment of an implant for the dynamic dorsal stabilization of a motion segment of the spinal column 12 is illustrated in FIGS. 6 to 11 and provided altogether with the reference numeral 110. Parts of the implant 110, which are of the same design or essentially the same design as parts of the implants 10 and 70, are provided with reference numerals which have the same two end numbers.

The implant 110 comprises an attachment device 114 which corresponds essentially to the attachment device 14. It comprises a tape 116 which can loop around the spinous processes 50 and 52 with its inner side 144 and be fixed to them. However, the tape 116, in contrast to the tape 16, is fixed to a central spacer element 134 at two attachment points 180 and 182. An upper part of the tape 116 runs around the spinous process 50, proceeding from the attachment point 180, in an anticlockwise direction when seen dorsally as far as the attachment point 182 which is provided on the spacer element 134 at the same level as the attachment point 180 but is spaced from it. The tape 116 therefore crosses over in the area of the spacer element 134 between the two attachment points 180 and 182 somewhat above them. The continued course of the tape proceeds from the attachment point 182 and runs around the spinous process 52 likewise in a counterclockwise direction as far as the attachment point 180. Consequently, the tape 116 crosses over itself again, namely between the attachment points 180 and 182 somewhat below them.

Analogously to the spacer elements 36 and 38, spacer elements 136 and 138 are also arranged at the spinous process receptacles 118 and 120 of the implant 110 so as to be located diametrically opposite the spacer element 134. The spacer element 134 differs from the spacer element 34 in that it is designed in two parts. A first spacer element part 134 has essentially the form of a reel, i.e., a cylindrical core with conical extensions adjoining it on both sides. Instead of a thread, the spacer element part 134a is enclosed by a second spacer element part 134b which is essentially of a sleeve-like design. As a result of the shape of the spacer element part 134a, the spacer element part 134b is provided with a circumferential recess 140, on which the spinous processes 50 and 52 can nestle. As a result of the two-part configuration and on account of its shape, an anisotropic spacer element 134 results altogether. Since the spacer element parts 134a and 134b are preferably produced from a hydrogel, the anisotropic structure of the spacer element 134 can be utilized, in particular, during an expansion and compression of the spacer element 134 for the dynamic adaptation of the motion segment, which is coupled by the implant 110, to the entire spinal column 12.

Figure 7:
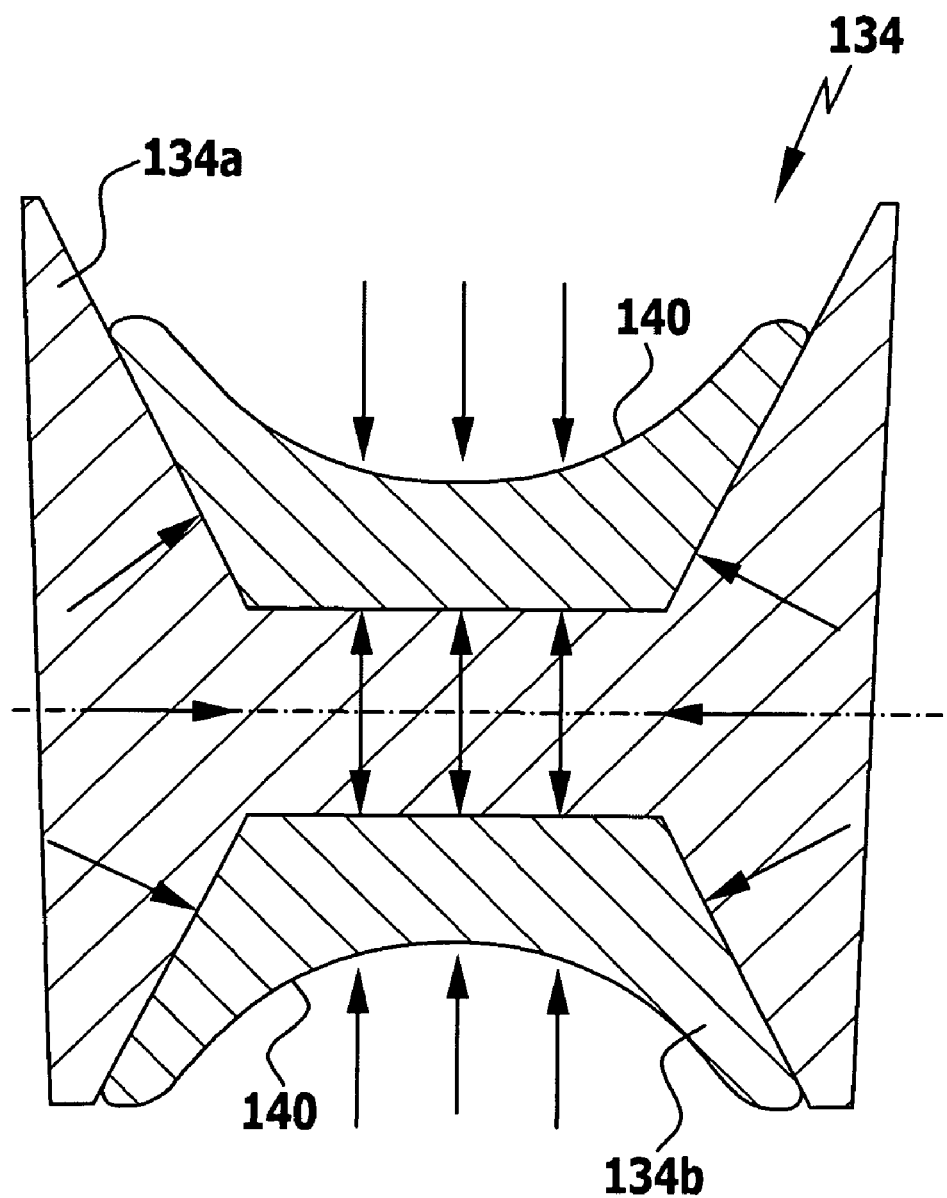
FIG. 7: shows a sectional view through an anisotropic spacer element illustrated in FIG. 6.
Figure 10:
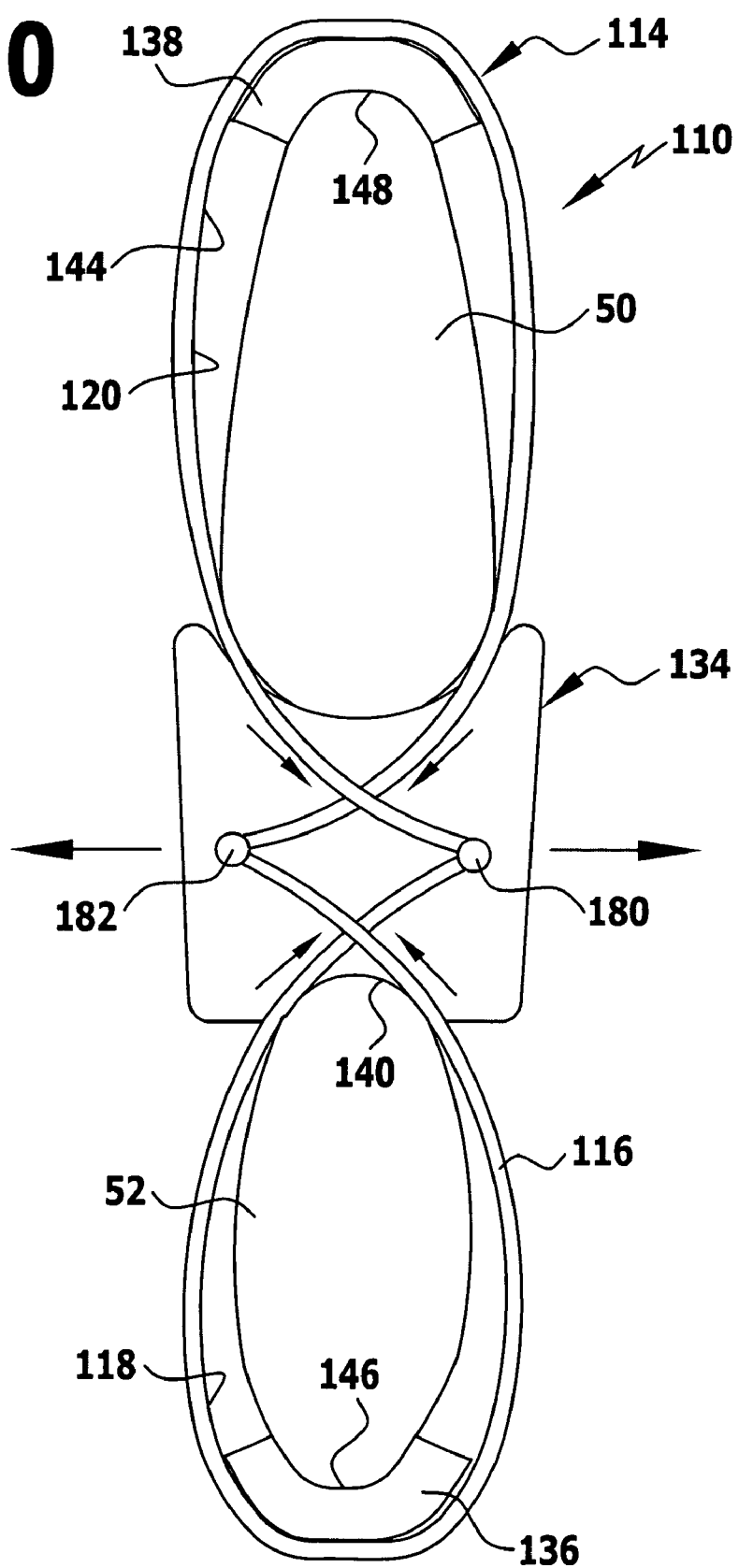
FIG. 10: shows a schematic illustration of the implant illustrated in FIG. 6 with spacer elements in the stabilizing position.

The result of the reel-like configuration of the spacer element part 134a is that a radial compression thereof results in an axial change in length, as indicated in FIG. 7 by the arrows. Such a change in length, for example, a shortening which can be designated as "muscle function", will be used to maintain a dynamic balance of the forces acting on the motion segment. In practice, this leads to the spacer element part 134b and the spacer element part 134a being compressed as a result of an increasing extension. If they are both produced from a hydrogel, they are partially dehydrated due to the action of the compression forces. If, for example, a radial compression of the spacer element part 134a is impeded by formation of an anisotropic structure thereof, this results in an axial shortening of the spacer element part 134a. This shortening, on the other hand, acts as a lateral compression on the spacer element part 134b and, therefore, counteracts an extension of the motion segment.

Instead of a two-part spacer element 134, a one-part spacer element can also be used which makes an axial shortening due to radial compression possible as a result of a corresponding, anisotropic construction.

The double crossover of the tape 116 has the following effect in the case of flexion of the motion segment: Tensioning of the tape 116, which acts on the entire implant 110, will be increased by an increase in the flexion. Since the spinous processes 50 and 52 press against the smaller spacer elements 136 and 138 during flexion, these spacer elements are increasingly dehydrated which can lead to a decrease in the tensioning of the tape 116. At the same time, however, the spacer element 134 arranged between the spinous processes 50 and 52 will be relieved of pressure and so it can expand laterally. On account of the crossover attachment of the tape 116 at the spacer element 134 at the attachment points 180 and 182, a lateral expansion of the spacer element 134 does, however, cause an increase in tension of the tape 116. In this way, the implant 110 can be adapted in an ideal manner to changes in the motion segment.

The implants described above can also each be equipped with only one single spacer element instead of with three spacer elements and this spacer element is arranged between the spinous processes 50 and 52 in the stabilizing position. The implants described provide, on the one hand, for a balance between movement and stability of the stabilized motion segment and restrict movement, in particular, any extension. Loads which act on the motion segment are partially absorbed by the spacer elements. As a result of a tension strapping formed by the respective attachment device, a relief of pressure on the intervertebral disk is achieved which is beneficial, in particular, for a regeneration of a partially degenerated intervertebral disk. In addition, the surface area of the foramen and of the spinal canal of the spinal column 12 is increased by the so-called kyphotic position. In the case of, for example, stenoses this is a mechanism which leads to the relief of pressure on the spinal cord and the cauda equina, respectively, or on the nerve roots. As a result of the relief of pressure on the motion segment by the implants described, it is possible to stop any further degeneration of the intervertebral disk with them or even partially regenerate it. An improved hydration of the intervertebral disk is, in particular, possible.

The tapes of the implants can be produced from woven or knitted polymer fibers. The spacer elements can, as already indicated, also be arranged in a textile pocket. Stability of the implant is increased, in particular, by a pocket as a result of a targeted reinforcement of the spacer elements. A fiber reinforcement of the spacer elements can also optimize a contact area between the spinous processes 50 and 52 and the spacer elements in order to minimize, for example, any abrasion of the spacer elements on the respective contact surface area.

As already described above, the spacer elements can also alter their external shape and/or their elastic properties anisotropically as a result of a change in ambient conditions and/or forces acting on them. Expansion during the hydration can, for example, be impeded in certain spatial directions. An anisotropic structure of the spacer elements can be created, for example, by a sandwich-like construction consisting of different layers. For this purpose, layers with a greater rigidity can, for example, be introduced into the softer structure of a hydrogel in order to specifically influence the overall rigidity of the hydrogel body. In this respect, textile layers, in particular, can be used.

A closure device serves to close the tape, as described above. Instead of the unidirectional closure described in the form of a cable tie, press clips can also be provided, for example, snap fasteners or free ends of the tape can simply be stitched together.

For the introduction of the implant, it will be preassembled, as described above, and brought into the implantation position, i.e., the spacer elements will be dehydrated when they are formed by hydrogels. The supraspinal ligament of the motion segment is retained, the interspinal ligament between the spinous processes will, however, be severed or penetrated obtusely. A distance between the spinous processes can be optionally measured with a measuring instrument or a test member and a corresponding implant size selected. The free ends of the tapes will be guided around the spinous processes 50 and 52 with a type of suture instrument. The spacer elements will be pushed in laterally under the supraspinal ligament, placed at the desired locations and possibly stitched to the interspinal or supraspinal ligament for an initial stable placement. Subsequently, the tape will be tensioned, for example, with a tensioning instrument for the defined pretensioning and the closure device closed, in particular, by pressing, clipping, suturing or closing of a cable tie closure.

After their implantation, the spacer elements consisting of hydrogel are hydrated as a result of the osmotic pressure in the extracellular space. The absorption of water can take several hours and the volume can increase by approximately 3 to 20 times. As a result of their expansion, the spacer elements adapt themselves to the anatomical structures of the spinous processes 50 and 52 in an ideal manner. Tensioning of the tape is increased by expansion of the outer, small spacer elements. In order to secure the implant until hydration is complete or a state of balance has been created, it may be fixed to the motion segment with preferably resorbable sutures.

The implants described above have, in particular, the property that they adapt themselves to a cyclic hydration and dehydration of the intervertebral disk in the manner described.

Instead of producing the spacer elements described from a hydrogel, memory materials can also be used, not only metals but also plastics, in particular, polymers, which alter their shape as a result of mechanical loads and, therefore, also their elastic properties.

What is claimed is:

1. Implant for the dorsal stabilization of a human or animal spinal column, comprising:
    an attachment device for at least one of placing in position against and fixing to spinous processes of adjacent vertebrae of the spinal column,
    at least one spacer element associated with the attachment device and designed in such a manner that it alters at least one of its external shape and its elastic properties as a result of a change in at least one of ambient conditions and forces acting on it,
    the attachment device comprising at least one tape adapted to be looped around at least one of the spinous processes, the at least one tape crossing over itself at least once in an area of the spacer element and being fixed to the spacer element at two spaced apart attachment points arranged on a back side of the spacer element.

2. Implant as defined in claim 1, wherein the spacer element is produced from a memory material.

3. Implant as defined in claim 2, wherein the memory material is a metal or a plastic.

4. Implant as defined in claim 1, wherein the spacer element is adapted to be hydrated.

5. Implant as defined in claim 4, wherein the at least one hydratable spacer element is produced at least partially from a hydrogel.

6. Implant as defined in claim 4, wherein the at least one spacer element is dehydrated in an implantation position of the implant, said implant being insertable into a human or animal body in said implantation position.

7. Implant as defined in claim 4, wherein the at least one spacer element is designed in such a manner that it is adapted to be hydrated in an extracellular space of a human or animal body on account of osmotic pressure.

8. Implant as defined in claim 4, wherein the at least one spacer element is designed in such a manner that it is adapted to be dehydrated at least partially as a result of pressure acting on it.

9. Implant as defined in claim 1, wherein the implant is adapted to be brought from an implantation position, said implant being adapted to at least one of be placed in position against the at least one spinous process and be released from said implantation position, into a stabilizing position, said implant being adapted to be fixed on the at least one spinous process in said stabilizing position.

10. Implant as defined in claim 9, wherein the at least one spacer element has at least one contact surface area for the spinous process and is designed in such a manner that the contact surface area for the spinous process abuts on at least one spinous process in the stabilizing position.

11. Implant as defined in claim 9, wherein the implant has at least one spinous process receptacle adapted to hold at least one of two spinous processes of two adjacent vertebrae in the stabilizing position.

12. Implant as defined in claim 11, wherein the at least one spinous process receptacle is open in the implantation position and closed in a ring shape in the stabilizing position.

13. Implant as defined in claim 11, wherein two spinous process receptacles are provided.

14. Implant as defined in claim 11, wherein a free cross-sectional surface area of the at least one spinous process receptacle becomes smaller with increasing hydration of the at least one spacer element.

15. Implant as defined in claim 11, wherein the at least one spacer element separates two spinous process receptacles from one another.

16. Implant as defined in claim 11, wherein at least two spacer elements are provided, said at least two spacer elements being arranged at a spinous process receptacle so as to be located diametrically opposite one another.

17. Implant as defined in claim 11, wherein the attachment device has at least one closure device and wherein the at least one spinous process receptacle is adapted to be opened in the implantation position and closed in a ring shape in the stabilizing position with the at least one closure device.

18. Implant as defined in claim 17, wherein the closure device is designed in the form of a unidirectional closure device, in particular, in the form of a cable tie closure.

19. Implant as defined in claim 17, wherein the closure device comprises a press clip.

20. Implant as defined in claim 1, wherein three spacer elements are provided.

21. Implant as defined in claim 1, wherein the at least one spacer element has in a basic position a volume at least 3 times smaller than a volume of the spacer element in a maximum expansion position.

22. Implant as defined in claim 21, wherein the at least one spacer element is dehydrated completely in the basic position and hydrated completely in the maximum expansion position.

23. Implant as defined in claim 1, wherein the at least one spacer element is deformable anisotropically so that it alters at least one of its shape and an enclosed volume anisotropically as a result of a change in at least one ambient condition.

24. Implant as defined in claim 23, wherein the at least one spacer element deformable anisotropically alters at least one of its shape and an enclosed volume anisotropically as a result of hydration.

25. Implant as defined in claim 1, wherein the at least one spacer element is symmetrically shaped.

26. Implant as defined in claim 1, wherein the at least one spacer element is designed and arranged on the attachment device in such a manner that it limits movement towards one another of spinous processes connected to one another.

27. Implant as defined in claim 1, wherein the at least one spacer element comprises at least two spacer element parts.

28. Implant as defined in claim 27, wherein the at least two spacer element parts are adapted to be anisotropically hydrated differently so that they alter at least one of their shape and an enclosed volume anisotropically as a result of hydration.

29. Implant as defined in claim 28, wherein the at least two spacer element parts are shaped and connected to one another in such a manner that they alter at least one of a shape and an enclosed volume in two directions linearly independent of one another as a result of hydration.

30. Implant as defined in claim 27, wherein the at least two spacer element parts are arranged in layers one on top of the other.

31. Implant as defined in claim 30, wherein the at least two spacer element parts arranged in layers one on top of the other are separated by layers of greater rigidity.

32. Implant as defined in claim 31, wherein the layers of greater rigidity comprise at least one of fabric layers and fiber-reinforced layers.

33. Implant as defined in claim 27, wherein a first spacer element part forms a core of the spacer element and wherein a second spacer element part surrounds the first spacer element part in a ring shape at least in sections.

34. Implant as defined in claim 1, wherein the at least one spacer element is designed in the form of a cushion.

35. Implant as defined in claim 1, wherein the at least one spacer element comprises a spacer element sleeve and a spacer element core and wherein the spacer element core alters at least one of its external shape and its elastic properties as a result of a change at least one of ambient conditions and forces acting on it.

36. Implant as defined in claim 35, wherein the spacer element sleeve is produced from a fabric.

37. Implant as defined in claim 35, wherein the spacer element sleeve is fiber-reinforced.

38. Implant as defined in claim 1, wherein the at least one tape is designed to extend in the form of a double loop in a stabilizing position.

39. Implant as defined in claim 1, wherein the at least one tape is produced from a woven material.

40. Implant as defined in claim 1, wherein the attachment device is designed in the form of a tension strapping limiting movement away from one another of spinous processes connected to one another.

41. Implant as defined in claim 1, wherein the at least one spacer element is connected non-detachably to the attachment device.

42. Implant as defined in claim 1, wherein:
the at least one tape is looped around two of the spinous processes of the adjacent vertebrae; and
the at least one tape crosses over itself twice in the area of the spacer element.

43. Implant as defined in claim 1, wherein the at least one tape overlaps itself at each of the two attachment points.

44. Implant system for the dorsal stabilization of a human or animal spinal column, comprising:
at least one implant for the dorsal stabilization of the spinal column, the at least one implant comprising:
an attachment device for placing in position against and/or fixing to spinous processes of adjacent vertebrae of the spinal column, and
at least one spacer element designed in such a manner that it alters at least one of its external shape and its elastic properties as a result of a change in at least one of ambient conditions and forces acting on it,
the attachment device comprising at least one tape adapted to be looped around at least one of the spinous processes, the at least one tape crossing over itself at least once in an area of the spacer element and being fixed to the spacer element at two spaced apart attachment points arranged on a back side of the spacer element, and instrumentation for inserting the implant into a human or animal body.

45. Implant system as defined in claim 44, wherein the implant is adapted to be brought from an implantation position, said implant being adapted to at least one of be placed in the implantation position against at least one spinous process of a vertebra of the spinal column and be released from said implantation position, into a stabilizing position, said implant being adapted to be fixed on the at least one spinous process in said position.

46. Method for the dorsal stabilization of a human or animal spinal column comprising:
opening up an access to the human or animal body, and
introducing an implant into the body with a spacer element of the implant dehydrated at least partially,
placing an attachment device for the implant in position against spinous processes of two adjacent vertebrae, and connecting the attachment device to the spinous processes at least loosely, wherein:

the at least one spacer element is designed in such a manner that it alters at least one of its external shape and its elastic properties as a result of a change in at least one of ambient conditions and forces acting on it, the attachment device comprising at least one tape adapted to be looped around at least one of the spinous processes, the at least one tape crossing over itself at least once in an area of the spacer element and being fixed to the spacer element at two spaced apart attachment points arranged on a back side of the spacer element, and instrumentation is provided for inserting the implant into the human or animal body.

47. Method as defined in claim 46, wherein a minimally invasive access is opened up.

* * * * *